United States Patent
Barth et al.

(10) Patent No.: US 7,879,902 B2
(45) Date of Patent: Feb. 1, 2011

(54) PYRROLE DERIVATIVES, INTERMEDIATES THEREFOR, PREPARATION AND THERAPEUTIC USE THEREOF

(75) Inventors: Francis Barth, Saint Georges d'Orques (FR); Christian Congy, Saint Gely du Fesc (FR); Laurent Hortala, Montpellier (FR); Murielle Rinaldi-Carmona, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 316 days.

(21) Appl. No.: 12/102,412

(22) Filed: Apr. 14, 2008

(65) Prior Publication Data

US 2008/0194581 A1 Aug. 14, 2008

Related U.S. Application Data

(63) Continuation of application No. 11/625,616, filed on Jan. 22, 2007, now Pat. No. 7,381,727, which is a continuation of application No. PCT/FR2005/002015, filed on Aug. 2, 2005.

(30) Foreign Application Priority Data

Aug. 9, 2004 (FR) .................................. 04 08773

(51) Int. Cl.
*A61K 31/4015* (2006.01)
*C07D 207/30* (2006.01)

(52) U.S. Cl. ...................... 514/423; 548/530; 548/537; 514/408

(58) Field of Classification Search ................. 548/530, 548/537; 514/408, 423
See application file for complete search history.

(56) References Cited

U.S. PATENT DOCUMENTS 7,381,727 B2 * 6/2008 Barth et al. ............ 514/254.01
7,524,971 B2 * 4/2009 Barth et al. ................. 548/563
7,618,995 B2 * 11/2009 Barth et al. ................. 514/427

FOREIGN PATENT DOCUMENTS

| EP | 0005156 | 11/1979 |
|---|---|---|
| EP | 0038536 | 10/1981 |
| WO | WO 97/19063 | 5/1997 |
| WO | WO 01/58869 | 8/2001 |
| WO | WO 03/007887 | 1/2003 |
| WO | WO 03/042174 | 5/2003 |
| WO | WO 03/063781 | 8/2003 |
| WO | WO 2004/026301 | 4/2004 |
| WO | WO 2004/058429 | 7/2004 |
| WO | WO 2004/060870 | 7/2004 |

OTHER PUBLICATIONS

Hauptmann et al (1972): STN International HCAPLUS database, (Columbus, Ohio), Accession No. 1972:551789.*
Handy, S.T., et. al., An Unusual Dehalogenation in the Suzuki Coupling of 4-Bromopyrrole-2-Carboxylates, Tetrahedron Letters, vol. 44, (2003) pp. 427-430.
Hemetsberger, H., et. al., Synthesis and Thermolysis of .alpha. - azido- .alpha. , .gamma. -dienoic esterss, Journal of Chemical Research, Synopses, vol. 10, (1977) pp. 247 abstract.

* cited by examiner

*Primary Examiner*—Golam M Shameem
(74) *Attorney, Agent, or Firm*—Balaram Gupta

(57) ABSTRACT

The invention concerns compounds of formula (I):

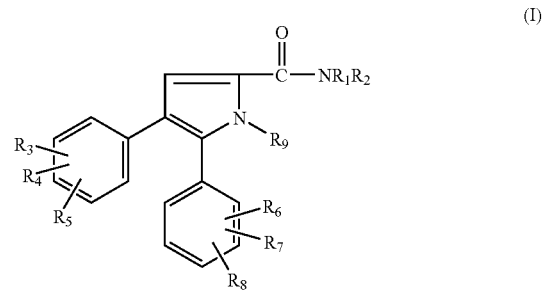

Wherein $R_1$, $R_2$, $R_3$, $R_4$, $R_5$, $R_6$, $R_7$, $R_8$ and $R_9$ are as defined herein. The invention also concerns the method for preparing said compounds including the intermediates therefor and their therapeutic use.

5 Claims, No Drawings

PYRROLE DERIVATIVES, INTERMEDIATES THEREFOR, PREPARATION AND THERAPEUTIC USE THEREOF

CROSS REFERENCE TO RELATED APPLICATIONS

This application is a continuation of U.S. application Ser. No. 11/625,616, filed Jan. 22, 2007, now allowed, which is a continuation of International application No. PCT/FR2005/002,015, filed Aug. 2, 2005, both of which are incorporated herein by reference in their entirety; which claims the benefit of priority of French Patent Application No. 04/08,773, filed Aug. 9, 2004.

BACKGROUND OF THE INVENTION

Field of the Invention

The present invention relates to 4,5-diphenylpyrrole-2-carboxamide derivatives, to their preparation and to their therapeutic application.

SUMMARY OF THE INVENTION

The present invention relates to compounds corresponding to the formula:

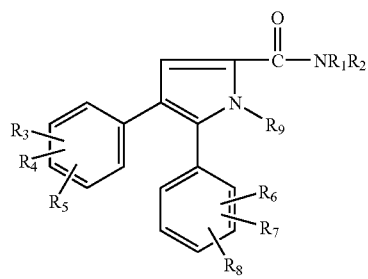

(I)

in which:
$R_1$ represents hydrogen or a $(C_1-C_4)$alkyl;
$R_2$ represents:
  a $(C_3-C_{10})$alkyl group, which is unsubstituted or substituted with a trifluoromethyl group;
  a non-aromatic $C_3-C_{12}$ carbocyclic radical, which is unsubstituted or substituted one or more times with a $(C_1-C_4)$alkyl, hydroxyl, cyano or $(C_1-C_4)$alkoxy group or a group $COR_{12}$;
  an indanyl;
  a 1,2,3,4-tetrahydro-1- or -2-naphthyl;
  a monooxygen or monosulfur heterocyclic radical of 5 to 7 atoms, which is unsubstituted or substituted one or more times with a $(C_1-C_4)$alkyl group;
  a mononitrogen heterocyclic radical of 5 to 7 atoms, which is unsubstituted or substituted one or more times with a $(C_1-C_4)$alkyl group, the nitrogen atom moreover being substituted with a $(C_1-C_4)$alkyl, phenyl, benzyl, $(C_1-C_4)$alkoxycarbonyl or $(C_1-C_4)$alkanoyl group, the phenyl or benzyl groups being unsubstituted or substituted one or more times with a halogen atom or a $(C_1-C_4)$alkyl, trifluoromethyl, hydroxyl or $(C_1-C_4)$alkoxy group;
  a benzothiophenyl or an indolyl, the said radicals being unsubstituted or substituted one or more times with a $(C_1-C_4)$alkyl group;
  a $(C_1-C_3)$alkylene group bearing a non-aromatic $C_3-C_{10}$ carbocyclic radical, which is unsubstituted or substituted one or more times with a $(C_1-C_4)$alkyl, hydroxyl, $(C_1-C_4)$alkoxy or cyano group or a group $COR_{12}$;
  a $(C_1-C_3)$alkylene group bearing a monooxygen, monosulfur or mononitrogen heteroaromatic or non-heteroaromatic heterocyclic radical of 5 to 7 atoms, which is unsubstituted or substituted one or more times with a $(C_1-C_4)$alkyl group;
  a $(C_1-C_3)$alkylene group bearing an indolyl or benzothiophenyl radical, the said radical being unsubstituted or substituted one or more times with a $(C_1-C_4)$alkyl group and the alkylene being unsubstituted or substituted with a hydroxyl, methyl or methoxy group or with a group $COR_{12}$;
  a $(C_1-C_3)$alkylene group bearing a $(C_1-C_4)$alkylthio group;
  a phenylalkylene group in which the alkylene is $(C_1-C_3)$, which is unsubstituted or substituted on the alkylene with one or more methyl, hydroxyl, hydroxymethyl, methoxy or methoxymethyl groups, or a group $COR_{12}$, and which is unsubstituted on the phenyl or substituted on the phenyl with one or more identical or different substituents chosen from a halogen atom and a $(C_1-C_4)$alkyl, trifluoromethyl, $(C_1-C_4)$alkoxy or trifluoromethoxy group;
  a benzhydryl or benzhydrylmethyl group;
  a group $NR_{10}R_{11}$;
or $R_1$ and $R_2$, together with the nitrogen atom to which they are attached, constitute:
  either a piperazin-1-yl or 1,4-diazepan-1-yl radical 4-substituted with a phenyl, benzyl, benzodioxolyl, benzodioxolylmethyl or tetrahydrofurylcarbonyl group or with a group $COR_{12}$ or $CH_2COR_{12}$;
  or a piperid-1-yl or pyrrolidin-1-yl radical mono- or gem-disubstituted with one or two groups chosen from a phenyl, benzyl, piperid-1-yl, pyrrolidin-1-yl, $(C_1-C_4)$alkyl, hydroxyl or cyano group and a group $COR_{12}$, $NR_{13}R_{14}$, $NHCOR_{15}$ or $CH_2COR_{12}$;
  the phenyl or benzyl groups being unsubstituted or substituted with one or more substituents independently chosen from a halogen atom, and a methyl, trifluoromethyl, hydroxyl or $(C_1-C_4)$alkoxy group;
$R_3$, $R_4$, $R_5$, $R_6$, $R_7$ and $R_8$ represent, independently of each other, a hydrogen or halogen atom, a $(C_1-C_6)$alkyl, $(C_1-C_6)$alkoxy or trifluoromethyl group or a group $S(O)_n$Alk;
$R_9$ represents a $(C_1-C_4)$alkyl group;
$R_{10}$ represents a hydrogen atom or a methyl group;
$R_{11}$ represents a $(C_3-C_6)$alkyl, phenyl or $(C_3-C_{10})$cycloalkyl group, the said phenyl and cycloalkyl groups being unsubstituted or substituted with one or more substituents independently chosen from a halogen atom and a $(C_1-C_4)$alkyl or trifluoromethyl group;
or $R_{10}$ and $R_{11}$, together with the nitrogen atom to which they are attached, constitute a saturated or unsaturated, bridged or non-bridged heterocyclic radical of 4 to 11 atoms, possibly comprising a spirane carbon and possibly containing a second hetero atom chosen from O and N, the said radical being unsubstituted or substituted one or more times with a hydroxyl, $(C_1-C_4)$alkyl or $(C_1-C_4)$alkoxycarbonyl group or with a phenyl group that is unsubstituted or substituted with one or more substituents independently chosen from a halogen atom and a ($C_1$-$C_4$)alkyl group;

$R_{12}$ represents a ($C_1$-$C_4$)alkyl, phenyl, benzyl, ($C_1$-$C_4$) alkoxy or trifluoromethyl group or a group $NR_{13}R_{14}$;

$R_{13}$ and $R_{14}$ each independently represent a hydrogen atom or a ($C_1$-$C_4$)alkyl group or, together with the nitrogen atom to which they are attached, constitute a radical chosen from azetidinyl, pyrrolidinyl, piperazinyl, piperidyl and azepinyl;

$R_{15}$ represents a ($C_1$-$C_4$)alkyl or trifluoromethyl group;

n represents 0, 1 or 2;

Alk represents a ($C_1$-$C_4$)alkyl group;

and also the salts, solvates and hydrates thereof.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. These salts are advantageously prepared with pharmaceutically acceptable acids, but the salts of other acids that are useful, for example, for purifying or isolating the compounds of formula (I) also form part of the invention.

The compounds according to the invention may also exist in the form of hydrates or solvates, i.e. in the form of associations or combinations with one or more water molecules or with a solvent. Such hydrates and solvates also form part of the invention.

More particularly, a subject of the present invention is compounds of formula (I) in which:

$R_1$ represents hydrogen or a ($C_1$-$C_4$)alkyl;

$R_2$ represents:
  a ($C_4$-$C_{10}$)alkyl group;
  a non-aromatic $C_3$-$C_{12}$ carbocyclic radical, which is unsubstituted or substituted one or more times with a ($C_1$-$C_4$)alkyl group;
  a 1,2,3,4-tetrahydro-1- or -2-naphthyl;
  a saturated monooxygen or monosulfur heterocyclic radical of 5 to 7 atoms, which is unsubstituted or substituted one or more times with a ($C_1$-$C_4$)alkyl group;
  a saturated mononitrogen heterocyclic radical of 5 to 7 atoms, the nitrogen atom being substituted with a ($C_1$-$C_4$)alkyl, phenyl, benzyl, ($C_1$-$C_4$)alkoxycarbonyl or ($C_1$-$C_4$)alkanoyl group;
  a ($C_1$-$C_3$)alkylene group bearing a non-aromatic $C_3$-$C_{10}$ carbocyclic radical, which is unsubstituted or substituted one or more times with a ($C_1$-$C_4$)alkyl group;
  a phenylalkylene group in which the alkylene is ($C_1$-$C_3$), which is unsubstituted or substituted on the alkylene with one or more methyl or ($C_1$-$C_4$)alkoxycarbonyl groups, and/or substituted on the phenyl with one or more identical or different substituents chosen from a halogen atom and a ($C_1$-$C_4$)alkyl, trifluoromethyl, ($C_1$-$C_4$)alkoxy or trifluoromethoxy group;
  a group $NR_{10}R_{11}$;
  or $R_1$ and $R_2$, together with the nitrogen atom to which they are attached, constitute either a piperazin-1-yl or 1,4-diazepan-1-yl radical 4-substituted with a phenyl or benzyl group; or a piperid-1-yl or pyrrolidin-1-yl radical mono- or gem-disubstituted with a phenyl, benzyl, ($C_1$-$C_4$)alkyl, hydroxyl, ($C_1$-$C_3$)alkanoyl, ($C_1$-$C_4$)alkoxycarbonyl or ($C_1$-$C_4$)alkoxycarbonylamino group; the phenyl or benzyl groups being unsubstituted or substituted one or more times with a halogen atom and/or a methyl group;

$R_3$, $R_4$, $R_5$, $R_6$, $R_7$ and $R_8$ represent, independently of each other, a hydrogen or halogen atom, a ($C_1$-$C_6$)alkyl, ($C_1$-$C_6$)alkoxy or trifluoromethyl group or a group $S(O)_n$ Alk;

$R_9$ represents a ($C_1$-$C_4$)alkyl group;

$R_{10}$ represents a hydrogen atom or a methyl group;

$R_{11}$ represents a ($C_3$-$C_6$)alkyl, phenyl or ($C_3$-$C_{10}$)cycloalkyl group, the said phenyl and cycloalkyl groups being unsubstituted or substituted with one or more halogen atoms and/or ($C_1$-$C_4$)alkyl groups;

or $R_{10}$ and $R_{11}$, together with the nitrogen atom to which they are attached, constitute a saturated or unsaturated, bridged or non-bridged heterocyclic radical of 5 to 11 atoms, possibly comprising a spirane carbon and possibly containing a second hetero atom chosen from O and N, the said radical being unsubstituted or substituted one or more times with a hydroxyl, ($C_1$-$C_4$)alkyl or ($C_1$-$C_4$) alkoxycarbonyl group; a phenyl group, which is unsubstituted or substituted with one or more halogen atoms or ($C_1$-$C_4$)alkyl groups;

n represents 0, 1 or 2;

Alk represents a ($C_1$-$C_4$)alkyl group;

and also the salts, solvates and hydrates thereof.

DETAILED DESCRIPTION OF THE INVENTION

The term "alkyl group" means a linear or branched radical such as, in particular: methyl, ethyl, propyl, isopropyl, butyl, isobutyl, tert-butyl, n-pentyl, isopentyl, n-hexyl, isohexyl, the methyl group being preferred for a ($C_1$-$C_4$)alkyl, and the tert-butyl, 2-methyl-2-butyl and 3,3-dimethyl-2-butyl groups being preferred for a ($C_4$-$C_{10}$)alkyl.

The term "alkylene group" means a linear divalent radical, methylene and ethylene being preferred.

The term "alkoxy group" means a linear or branched radical, the methoxy group being preferred.

The term "halogen atom" means a fluorine, chlorine, bromine or iodine atom; fluorine, chlorine or bromine atoms being preferred.

The non-aromatic $C_3$-$C_{12}$ carbocyclic radicals comprise bridged or fused monocyclic or polycyclic radicals. The monocyclic radicals include cycloalkyls, for example cyclopropyl, cyclobutyl, cyclopentyl, cyclohexyl, cycloheptyl and cyclooctyl; cyclohexyl and cyclopentyl being preferred. The fused, bridged or spirane bicyclic or tricyclic radicals include, for example, norbornyl, bornyl, isobornyl, noradamantyl, adamantyl, spiro[5.5]undecanyl, bicyclo[2.2.1]heptanyl, bicyclo[3.2.1]octanyl and bicyclo[3.1.1]heptanyl radicals.

The term "saturated or unsaturated heterocyclic radical of 4 to 11 atoms, possibly containing a second hetero atom such as O or N" means radicals such as morpholin-4-yl, piperid-1-yl, piperazin-1-yl, pyrrolidin-1-yl or octahydrocyclopenta[c]pyrrol-2-yl, the piperid-1-yl and morpholin-4-yl radicals being preferred.

The term "mononitrogen heterocyclic radical of 5 to 7 atoms" means a radical such as piperid-4-yl or pyrrolidin-3-yl, the piperid-4-yl radical being preferred.

The term "monooxygen heterocyclic radical of 5 to 7 atoms" means a radical such as tetrahydrofuryl, tetrahydro-2H-pyranyl or oxepanyl; tetrahydrofuryl being preferred.

The term "monosulfur heterocyclic radical of 5 to 7 atoms" means a radical such as tetrahydrothiophenyl or tetrahydrothiopyranyl.

The term "heteroaromatic heterocyclic radical of 5 to 7 atoms" means a radical such as pyridyl, pyrrolyl, thiophenyl or furanyl.

According to the present invention, the compounds of formula (I) that are preferred are those in which:
- $R_1$ represents hydrogen and $R_2$ represents a group $NR_{10}R_{11}$ in which $R_{10}$ and $R_{11}$, together with the nitrogen atom to which they are attached, constitute a saturated heterocyclic radical of 5 to 11 carbon atoms, which is unsubstituted or substituted one or more times with a $(C_1-C_4)$ alkyl;
- or $R_1$ and $R_2$, together with the nitrogen atom to which they are attached, constitute a piperid-1-yl radical gem-disubstituted with a phenyl, benzyl, pyrrolidin-1-yl or piperid-1-yl group and with a cyano, $(C_1-C_3)$alkanoyl or aminocarbonyl group;
- or $R_1$ and $R_2$ together represent a piperazin-1-yl group 4-substituted with a benzyl, which is itself unsubstituted or substituted with a halogen atom;
- and/or $R_3$, $R_4$, $R_5$, $R_6$, $R_7$ and $R_8$ represent, independently of each other, a hydrogen or halogen atom or a methoxy group;
- $R_9$ represents a $(C_3-C_4)$alkyl group;

and also the salts, solvates and hydrates thereof.

The compounds of formula I that are distinguished in particular are those in which:
- $R_1$ represents hydrogen and $R_2$ represents a piperid-1-yl radical or a $(C_1-C_3)$alkylene radical substituted with a phenyl and with a methoxy or methoxycarbonyl group;
- or $R_1$ and $R_2$, together with the nitrogen atom to which they are attached, represent a piperid-1-yl radical 4-gem-disubstituted with a phenyl or piperid-1-yl group and with an acetyl, aminocarbonyl or cyano group;
- or $R_1$ and $R_2$ together represent a piperazin-1-yl group 4-substituted with a benzyl, which is itself unsubstituted or substituted with a halogen atom;
- $R_6$ is a 4-chloro or a 4-methoxy and $R_3$ and $R_4$ represent 2,4-dichloro or 2-chloro, $R_5$, $R_7$ and $R_8$ representing a hydrogen atom;
- $R_9$ represents a methyl group;

and also the salts, solvates and hydrates thereof.

Among the compounds of the invention that may especially be mentioned are the following compounds:
- 4-(2,4-dichlorophenyl)-5-(4-methoxyphenyl)-1-methyl-N-piperid-1-yl-1H-pyrrole-2-carboxamide;
- 5-(4-chlorophenyl)-4-(2,4-dichlorophenyl)-1-methyl-N-piperid-1-yl-1H-pyrrole-2-carboxamide;
- 1-(1-((5-(4-chlorophenyl)-4-(2,4-dichlorophenyl)-1-methyl-1H-pyrrol-2-yl)carboxyl)-4-phenylpiperid-4-yl)ethanone;
- 1-{[4-(2-chlorophenyl)-5-(4-chlorophenyl)-1-methyl-1H-pyrrol-2-yl]carbonyl}-4-phenylpiperidine-4-carbonitrile;
- 1-(4-chlorobenzyl)-4-{[4-(2-chlorophenyl)-5-(4-chlorophenyl)-1-methyl-1H-pyrrol-2-yl]carbonyl}-piperazine;
- N-(1-benzyl-2-methoxyethyl)-4-(2-chlorophenyl)-5-(4-chlorophenyl)-1-methyl-1H-pyrrole-2-carboxamide;
- methyl 1-{[4-(2-chlorophenyl)-5-(4-chlorophenyl)-1-methyl-1H-pyrrol-2-yl]carbonyl}-α-methylphenylalaninate;
- 1'-{[5-(4-chlorophenyl)-4-(2,4-dichlorophenyl)-1-methyl-1H-pyrrol-2-yl]carbonyl}-1,4'-bipiperidine-4'-carboxamide;

and also the salts, solvates and hydrates thereof.

A subject of the present invention is also a process for preparing the compounds according to the invention.

This process is characterized in that the acid of formula (II) or a functional derivative of this acid of formula:

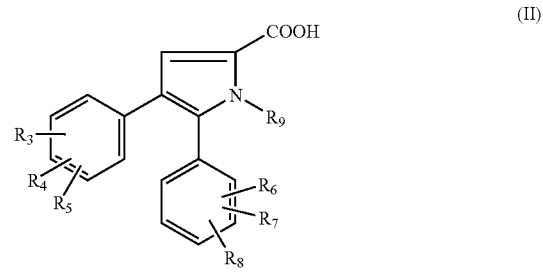

(II)

in which $R_3$, $R_4$, $R_5$, $R_6$, $R_7$, $R_8$ and $R_9$ are as defined for (I) is treated with an amine of formula $HNR_1R_2$ (III) in which $R_1$ and $R_2$ are as defined for (I). The compound thus obtained is optionally converted into a salt or solvate thereof.

Functional derivatives of the acid (II) that may be used include the acid chloride, the anhydride, a mixed anhydride, a $(C_1-C_4)$alkyl ester in which the alkyl is straight or branched, a benzyl ester, an activated ester, for example the p-nitrophenyl ester, or the suitably activated free acid, for example activated with N,N-dicyclohexylcarbodiimide or with benzotriazol-1-yloxotris(dimethylamino)phosphonium hexafluorophosphate (BOP) or benzotriazol-1-yloxotris(pyrrolidino)phosphonium hexafluorophosphate (PyBOP).

Thus, in the process according to the invention, the 1,3-oxazole-3-carboxylic acid chloride, obtained by reacting thionyl chloride with the acid of formula (II), may be reacted with an amine $HNR_1R_2$, in an inert solvent, such as a chlorinated solvent (for example dichloromethane, dichloroethane or chloroform), an ether (for example tetrahydrofuran or dioxane) or an amide (for example N,N-dimethylformamide) under an inert atmosphere, at a temperature of between 0° C. and the ambient or super-ambient temperature, in the presence of a tertiary amine such as triethylamine, N-methylmorpholine or pyridine.

One variant consists in preparing the mixed anhydride of the acid of formula (II) by reacting ethyl chloroformate with the acid of formula (II), in the presence of a base such as triethylamine, and in reacting it with an amine $HNR_1R_2$, in a solvent such as dichloromethane, under an inert atmosphere, at room temperature, in the presence of a base such as triethylamine.

The compounds of formula (II) may be prepared according to the following scheme:

SCHEME 1

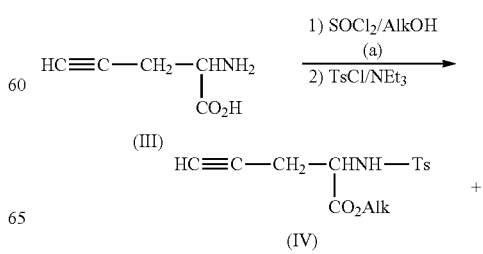

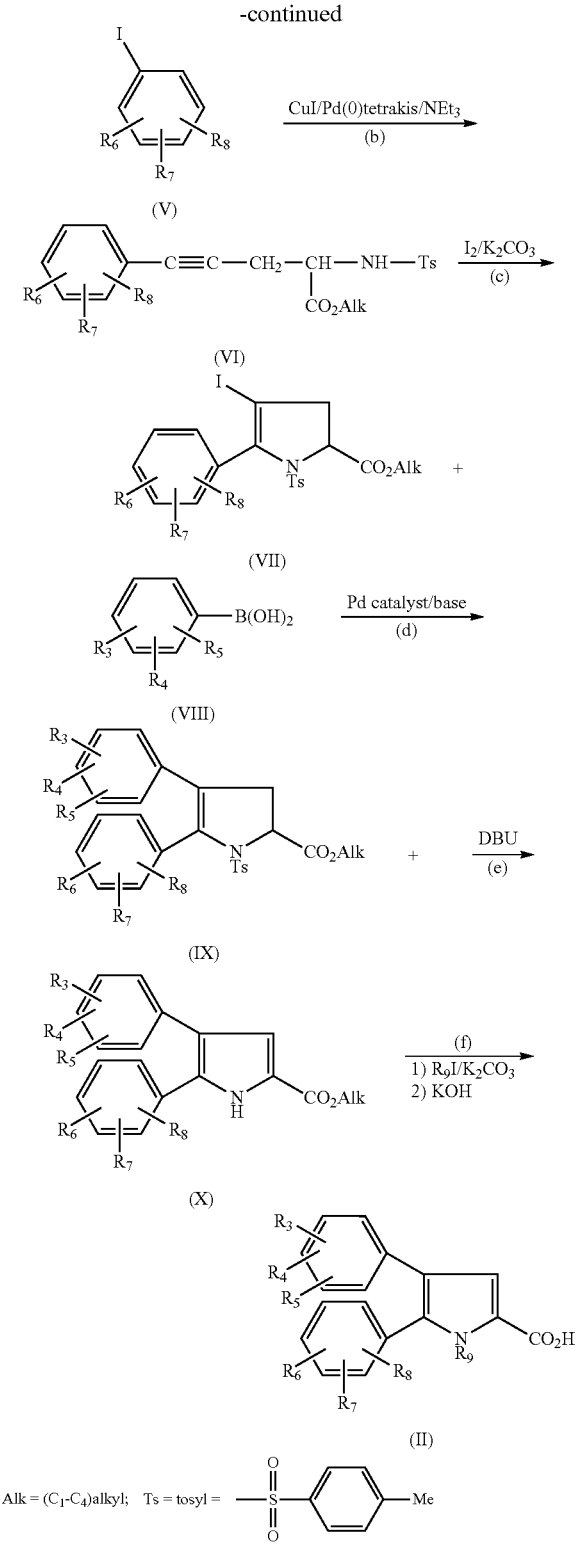

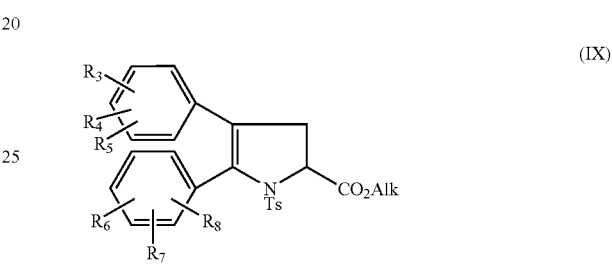

The preparation of the dihydropyrrole derivative of formula (VII) via steps a), b) and c) is performed according to J. Chem. Soc. Perkin Trans. 1, 2002, 622-628, which is incorporated by reference in its entirety.

The substitution of the dihydropyrrole nucleus with a substituted phenyl group is performed in step d) via the action of a substituted phenylboronic acid of formula (VIII) in the presence of a palladium catalyst such as tetrakis(triphenylphosphine)Pd(0), bisdibenzylideneacetonepalladium(0) [Pd(dba)$_2$], tris(dibenzylideneacetone)dipalladium(0), palladium acetate Pd(II) [Pd(OCOCH$_3$)$_2$], dichloro(diphenylphosphinoferrocene)Pd(II) [PdCl$_2$dppf], and in the presence of a base.

In step e) the tosyl protecting group on the nitrogen is removed via the action of a diamine such as DBU (1,8-diazabicyclo[5.4.0]undecene), and the pyrrole nucleus is simultaneously aromatized.

In step f), the pyrrole nitrogen is alkylated via the action of an alkyl iodide of formula R$_9$I, and the ester of formula (X) is then hydrolyzed in basic medium to obtain the acid of formula (II).

The compounds of formulae (IX), (X) and (II) are novel.

A subject of the present invention is also the compounds of formula:

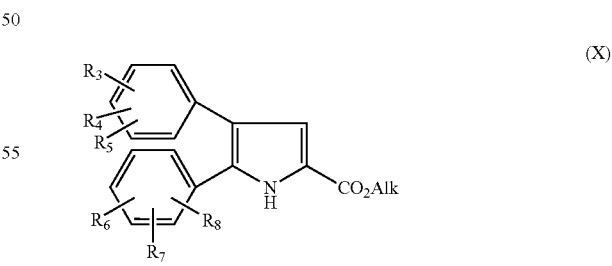

in which:

R$_3$, R$_4$, R$_5$, R$_6$, R$_7$ and R$_8$ represent, independently of each other, a hydrogen or halogen atom, a (C$_1$-C$_6$)alkyl, (C$_1$-C$_6$)alkoxy or trifluoromethyl group or a group S(O)$_n$Alk;

Ts represents a tosyl group;

Alk represents a (C$_1$-C$_4$)alkyl group;

n represents 0, 1 or 2.

Certain esters of formula (X) are described in the literature: the methyl and ethyl esters of 4,5-diphenyl-1H-pyrrole-2-carboxylic acid are described in J. Chem. Research, synopses, 1977, 10, 247; the ethyl ester of 1H-pyrrole-5-(4-methoxyphenyl)-4-phenyl-2-carboxylic acid is described in Tetrahedron Letters, 2003, 44(3), 427-430; both of these references are incorporated herein by reference in their entirety.

A subject of the present invention is also the compound of formula:

in which:

R$_3$, R$_4$, R$_5$, R$_6$, R$_7$ and R$_8$ represent, independently of each other, a hydrogen or halogen atom, a (C$_1$-C$_6$)alkyl, (C$_1$-C$_6$)alkoxy or trifluoromethyl group or a group S(O)$_n$Alk on condition that R$_3$, R$_4$, R$_5$, R$_6$, R$_7$ and R$_8$ do not simultaneously represent hydrogen, and on condition that when $R_6$ is a 4-methoxy group, $R_3$, $R_4$, $R_5$, $R_7$ and $R_8$ do not simultaneously represent hydrogen;

Alk represents a $(C_1-C_4)$alkyl group, n represents 0, 1 or 2.

A subject of the present invention is also the compounds of formula:

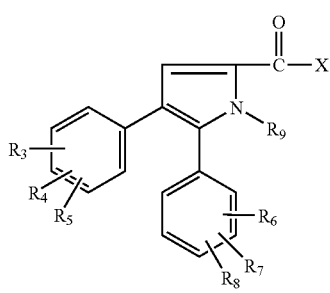

(IIa)

in which:

X represents a halogen atom or a hydroxyl, $(C_1-C_4)$alkoxy or benzyloxy group;

$R_3$, $R_4$, $R_5$, $R_6$, $R_7$ and $R_8$ represent, independently of each other, a hydrogen or halogen atom, a $(C_1-C_6)$alkyl, $(C_1-C_6)$alkoxy or trifluoromethyl group or a group $S(O)_n$ Alk;

$R_9$ represents a $(C_1-C_4)$alkyl;

Alk represents a $(C_1-C_4)$alkyl;

n represents 0, 1 or 2.

When X represents an OH group, the compounds of formula (IIa) may also exist in the form of salts. Such salts form part of the invention.

According to the present invention, 5-(4-chlorophenyl)-4-(2,4-dichlorophenyl)-1-methyl-1H-pyrrole-2-carboxylic acid, 4-(2,4-dichlorophenyl)-5-(4-methoxyphenyl)-1-methyl-1H-pyrrole-2-carboxylic acid, and 4-(2-chlorophenyl)-5-(4-chlorophenyl)-1-methyl-1H-pyrrole-2-carboxylic acid, and the methyl and ethyl esters thereof, and the chlorides thereof, are preferred.

The amines of formula $HNR_1R_2$ (III) are known or prepared via known methods.

The examples that follow describe the preparation of certain compounds in accordance with the invention. These examples are not limiting and serve merely to illustrate the present invention. The numbers of the compounds given as examples refer to those given in the table below, which illustrates the chemical structures and the physical properties of a number of compounds according to the invention.

In the examples, the following abbreviations are used:

m.p.: melting point

PyBOP: benzotriazol-1-yloxotris(pyrrolidino)phosphonium hexafluorophosphate

TBTU: 2-(1H-benzotriazol-1-yl)-1,1,3,3-tetramethyluronium tetrafluoroborate

DIPEA: diisopropylethylamine

RT: room temperature

EtOAc: ethyl acetate

MeOH: methanol

DMF: N,N-dimethylformamide.

The nuclear magnetic resonance spectra are recorded at 200 MHz in DMSO-$d_6$. For the interpretation of the spectra, the following abbreviations are used: s: singlet, d: doublet, t: triplet, m: unresolved complex, mt: multiplet, bs: broad singlet, dd: doubled doublet.

The compounds according to the invention are analyzed by LC/UV/MS coupling (liquid chromatography/UV detection/mass spectrometry). The molecular peak (MH⁺) and the retention time (rt) in minutes are measured.

Conditions A

A Symmetry C18 2.1×50 mm, 3.5 μm column is used, at 30° C., flow rate 0.4 mL/minute.

The eluent is composed as follows:

solvent A: 0.005% trifluoroacetic acid (TFA) in water at pH 3.15;

solvent B: 0.005% TFA in acetonitrile.

Gradient:

| Time (minutes) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C., flow rate 0.4 ml/minute.

The UV detection is performed at λ=210 nm and the mass detection in positive ESI chemical ionization mode.

Conditions MS5

An XTERRA MS C18 2.1×30 mm, 3.5 μm column is used, flow rate 1 ml/minute.

The eluent is composed as follows:

solvent A: 0.025% TFA in water, solvent B: 0.025% TFA in acetonitrile.

Gradient

| Time (minutes) | % A | % B |
|---|---|---|
| 0 | 100 | 0 |
| 2 | 0 | 100 |
| 2.7 | 0 | 100 |
| 2.75 | 100 | 0 |

The UV detection is performed via an iodine array detector between 210 and 400 nm and the mass detection in positive ESI mode.

Preparation 1

A) Methyl 2-(((4-methylphenyl)sulfonyl)amino)pent-3-ynoate 2.5 g of 2-amino-3-butynoic acid are suspended in 45 ml of methanol at 0° C. 1.8 ml of thionyl chloride are added dropwise at this temperature and the mixture is then refluxed for 3 hours. The solution is concentrated and the residue is dried under reduced pressure. The resulting material is dissolved in 60 ml of acetonitrile followed by 5.4 ml of triethylamine, and 4.6 g of tosyl chloride are then added. The mixture is stirred at room temperature for 19 hours and then at 50° C. for a further one hour. After concentrating, the crude material is dissolved in dichloromethane and the organic phase is successively washed with saturated aqueous $KHSO_4$ solution and then with K₂CO₃. The organic phase is dried over magnesium sulfate and then filtered and finally concentrated to give 5.18 g of the expected compound.

¹H NMR: δ (ppm): 2.35: s: 3H; 2.45: m: 2H; 3.45: s: 3H; 3.9: dd: 1H; 7.35: d: 2H; 7.65: d: 2H; 8.4: d: 1H.

B) Methyl 5-(4-chlorophenyl)-2-(4-tosylsulfonyl-amino)pent-4-ynoate 1 g of the compound from the preceding step and 0.57 g of 4-chloroiodobenzene are dissolved in 20 ml of anhydrous DMF. The solution is degassed under vacuum for 30 minutes. 0.64 ml of triethylamine is then added, followed by addition of 0.28 g of tetrakis(triphenylphosphine)palladium(0) and 0.1 g of copper iodide. The mixture is stirred at room temperature under an argon atmosphere for 19 hours. The crude reaction material is concentrated and purified by chromatography on silica gel using cyclohexane/ethyl acetate (80/20; v/v) as eluent. 1 g of the compound is recovered.

¹H NMR: δ (ppm): 2.35: s: 3H; 2.70-2.80: m: 2H; 3.45: s: 3H; 4.05: dd: 1H; 7.35: m: 4H; 7.4: d: 2H; 7.65: d: 2H; 8.51: d: 1H.

C) Methyl 5-(4-chlorophenyl-4-iodo-1-(4-tosyl-sulfonyl)-2,3-dihydro-1H-pyrrole-2-carboxylate 1 g of the compound obtained in the preceding step is dissolved in 5 ml of anhydrous acetonitrile in the presence of 1 g of potassium carbonate at 0° C. 2 g of solid iodine are added in several small fractions with stirring at this temperature. The mixture is allowed to return to room temperature over 24 hours. The reaction is stopped with sodium thiosulfate solution until decolorized, and the organic phase is extracted with dichloromethane. After drying over magnesium sulfate, filtering and concentrating, 1.27 g of the expected compound are obtained.

LC/MS (conditions A): M=517, rt=10.8 minutes.

D) Methyl 5-(4-chlorophenyl)-4-(2,4-dichlorophenyl)-1-tosylsulfonyl-2,3-dihydro-1H-pyrrole-2-carboxylate 15 g of the compound obtained in the preceding step and 6.8 g of 2,4-dichlorophenylboronic acid are dissolved in a mixture of 150 ml of methanol and 710 ml of toluene in the presence of 48 ml of sodium carbonate solution (2N). The reaction medium is left under argon for 30 minutes and 4.7 g of tetrakis(triphenylphosphine)palladium(0) are then added. The solution is heated at 60° C. for 4 hours under an inert atmosphere. After cooling, the crude product is concentrated and purified by chromatography on silica gel in toluene. 9.7 g of the expected compound are obtained in the form of a white powder.

¹H NMR: δ (ppm): 2.4: s: 3H; 2.75-2.95: m: 1H; 3.8: s: 3H; 5.15: d: 1H; 6.7: d: 1H; 7.1-7.7: m: 6H.

E) Methyl 5-(4-chlorophenyl)-4-(2,4-dichlorophenyl)-1H-pyrrole-2-carboxylate 9.7 g of the compound obtained in the preceding step are dissolved in 60 ml of anhydrous N,N-dimethylformamide. 5.4 ml of DBU (1,8-diazabicyclo[5.4.0]undecene) are then added and the mixture is heated at 100° C. for 24 hours. The crude product is concentrated and, after addition of ethanol, a white precipitate appears. This precipitate is filtered off, and 6 g of the expected compound are collected.

¹H NMR: δ (ppm): 3.8: s: 3H; 6.9: s: 1H; 7.2: s: 1H; 7.25: s: 2H; 7.3-7.4: m: 3H; 7.65: dd: 1H; 12.4: s: 1H.

F) 5-(4-Chlorophenyl)-4-(2,4-dichlorophenyl)-1-methyl-1H-pyrrole-2-carboxylic acid 5.9 g of the compound obtained in the preceding step are dissolved in 150 ml of DMF and 3.5 g of potassium carbonate are added. At room temperature, 1.5 ml of iodomethane are added to the mixture and the reaction is left for 24 hours. The solution is filtered and the filtrate is evaporated to dryness and then dissolved in 430 ml of methanol, and 7 ml of water are added, followed by addition of 8.7 g of potassium hydroxide pellets. The mixture is refluxed for 24 hours. After concentrating, the solid obtained is washed with ether and then dissolved in dichloromethane. The organic phase is treated with aqueous hydrochloric acid solution (10%). The organic phase is then dried over magnesium sulfate and then filtered and concentrated. 5.8 g of the expected compound are collected in the form of a white solid, m.p.=194° C.

¹H NMR: δ (ppm): 3.75: s: 3H; 6.9: s: 2H; 7.05: dd: 2H; 7.15-7.30: m: 3H; 7.45: d: 2H; 7.55: dd: 1H; 12.5: s: 1H.

The following acids of formula (I) are prepared in the same manner:

5-(4-Chlorophenyl)-4-(2-dichlorophenyl)-1-methyl-1H-pyrrole-2-carboxylic acid m.p.=190° C.
LC/MS (conditions A): MH⁺: 346, rt=7.77 min
¹H NMR: δ (ppm): 3.75: s: 3H; 6.9: s: 1H; 7.05-7.3: m: 5H; 7.35-7.50: m: 3H; 12.5: s: 1H.

5-(4-Methoxyphenyl)-4-(2,4-dichlorophenyl)-1-methyl-1H-pyrrole-2-carboxylic acid LC/MS (conditions A): MH⁺: 376, rt=10.24 min

Example 1

Compound 2

5-(4-Chlorophenyl)-4-(2,4-dichlorophenyl)-1-methyl-N-piperid-1-yl-1H-pyrrole-2-carboxamide 0.8 g of the compound of Preparation 1 are dissolved in 15 ml of dichloromethane, and 0.7 ml of triethylamine is added, followed by addition of 0.27 ml of N-aminopiperidine and then 1.31 g of PyBOP, and the mixture is stirred at room temperature for 24 hours. The crude reaction product is concentrated and the compound precipitates from a cyclohexane/ethyl acetate mixture (80/20). 0.46 g of the expected compound is obtained. m.p.=218° C.

Example 2

The compounds of formula (I) described in Table 2 are prepared by combinatorial chemistry according to the process described below:

the carboxylic acids of formula (III) are dissolved in DMF at a concentration of 0.25M in the presence of 3 equivalents of DIPEA. 120 μl of this solution and 120 μl of a solution of TBTU in DMF at a concentration of 0.25M are placed in each 2-ml well. 300 μl of a solution containing the amine of formula (III) in DMF at a concentration of 0.1M and 3 equivalents of DIPEA are added to each well. The plates are agitated at r.t. for 16 hours and then evaporated. The products formed are dissolved in each well with 500 µl of EtOAc, 400 µl of 0.1M $Na_2CO_3$ are added and the plates are agitated. After separation of the phases by settling, 430 µl of aqueous phase are discarded and 300 µl of 5% NaCl are then added, and the plates are agitated. 350 µl of aqueous phase are then discarded and the residues are analyzed by LC/UV/MS (conditions MS5).

The tables that follow illustrate the chemical structures and the physical properties of a number of compounds according to the invention.

In these tables, Et, Me, nPr and tBu mean, respectively, ethyl, methyl, n-propyl and tert-butyl.

TABLE 1

(I)

| Compound No. | $R_6$ | $-NR_1R_2$ | Characterization m.p. ° C. |
|---|---|---|---|
| 1 | Cl | (N-piperidinyl with 4-phenyl, 4-COMe) | 197° C. |
| 2 | Cl | —NH—N(piperidine) | 218° C. |
| 3 | OMe | —NH—N(piperidine) | 180° C. |
| 4 | Cl | N-methylpiperidine-4-(N-piperidinyl)-4-C(O)NH$_2$ | 265° C. (hydrochloride) |
| 5 | Cl | N-methylpiperidine-4-(N-pyrrolidinyl)-4-C(O)NH$_2$ | 183° C. |

TABLE 2

(I)

| Compound No. | $R_3, R_4$ | $R_6, R_7$ | $NR_1R_2$ | Characterization Condition |
|---|---|---|---|---|
| 6 | 2,4-diCl | 4-Cl | piperazinyl-CH$_2$-benzodioxole | MH$^+$ = 581.8 rt = 1.79 MS5 |

TABLE 2-continued (I)

| Compound No. | R₃, R₄ | R₆, R₇ | NR₁R₂ | Characterization Condition |
|---|---|---|---|---|
| 7 | 2,4-diCl | 4-Cl | —NH—C*H(CH₂—OMe)—CH₂—phenyl  Chiral (S) | MH⁺ = 526.9<br>rt = 2.31<br>MS5 |
| 8 | 2,4-diCl | 4-Cl | —NH—CH(Me)—(4-Cl-phenyl)  racemic | MH⁺ = 516.8<br>rt = 2.35<br>MS5 |
| 9 | 2,4-diCl | 4-Cl | —NH—CH₂—CH₂—tBu | MH⁺ = 463.0<br>rt = 2.36<br>MS5 |
| 10 | 2,4-diCl | 4-Cl | N-methyl-4-ethyl-4-phenylpiperidinyl | MH⁺ = 550.9<br>rt = 2.58<br>MS5 |
| 11 | 2,4-diCl | 4-Cl | —NH-norbornyl (endo) | MH⁺ = 486.9<br>rt = 2.49<br>MS5 |
| 12 | 2,4-diCl | 4-Cl | N-methyl-4-benzoylpiperidinyl | MH⁺ = 550.9<br>rt = 2.30<br>MS5 |
| 13 | 2,4-diCl | 4-Cl | N-methyl-4-(3-CF₃-phenyl)-4-(C(O)NHMe)piperidinyl | MH⁺ = 647.8<br>rt = 2.27<br>MS5 |
| 14 | 2,4-diCl | 4-Cl | —NH-indan-2-yl | MH⁺ = 494.9<br>rt = 2.37<br>MS5 |

TABLE 2-continued (I)

| Compound No. | R₃, R₄ | R₆, R₇ | NR₁R₂ | Characterization Condition |
|---|---|---|---|---|
| 15 | 2,4-diCl | 4-Cl | (1-methylpiperidin-4-yl with CN and phenyl substituents at C4) | MH⁺ = 547.9<br>rt = 2.30<br>MS5 |
| 16 | 2,4-diCl | 4-Cl | (4-methylpiperazin-1-yl)-CH₂-(4-Cl-phenyl) | MH⁺ = 571.9<br>rt = 1.83<br>MS5 |
| 17 | 2,4-diCl | 4-Cl | (1-methylpiperidin-4-yl with C(O)nPr and phenyl substituents at C4) | MH⁺ = 592.9<br>rt = 2.49<br>MS5 |
| 18 | 2,4-diCl | 4-Cl | (1-methylpiperidin-4-yl with C(O)OMe and 3-CF₃-phenyl substituents at C4) | MH⁺ = 648.9<br>rt = 2.43<br>MS5 |
| 19 | 2,4-diCl | 4-Cl | —NH—(2,2,5,5-tetramethyltetrahydrofuran-3-yl) | MH⁺ = 504.9<br>rt = 2.21<br>MS5 |
| 20 | 2,4-diCl | 4-Cl | 4-(4-chlorophenyl)piperazin-1-yl | MH⁺ = 557.8<br>rt = 2.44<br>MS5 |
| 21 | 2,4-diCl | 4-Cl | 4-(3-trifluoromethylphenyl)piperazin-1-yl | MH⁺ = 591.8<br>rt = 2.44<br>MS5 |
| 22 | 2,4-diCl | 4-Cl | —NH—CH(Me)—phenyl<br>racemic | MH⁺ = 482.9<br>rt = 2.33<br>MS5 |

TABLE 2-continued (I)

| Compound No. | R₃, R₄ | R₆, R₇ | NR₁R₂ | Characterization Condition |
|---|---|---|---|---|
| 23 | 2,4-diCl | 4-Cl | —NH—CH₂—CH(C₆H₅)₂ | MH⁺ = 558.9<br>rt = 2.38<br>MS5 |
| 24 | 2,4-diCl | 4-Cl | —NH—C(Me)₂—CH₂—Ph | MH⁺ = 510.9<br>rt = 2.44<br>MS5 |
| 25 | 2,4-diCl | 4-Cl | N-methyl-4-hydroxy-4-phenylpiperidinyl | MH⁺ = 538.9<br>rt = 2.18<br>MS5 |
| 26 | 2,4-diCl | 4-Cl | —NH—(CH₂)₃—Ph | MH⁺ = 496.9<br>rt = 2.38<br>MS5 |
| 27 | 2-Cl | 4-Cl | —NH—(CH₂)₂—(1H-indol-3-yl) | MH⁺ = 487.9<br>rt = 2.40<br>MS5 |
| 28 | 2-Cl | 4-Cl | 4-methyl-1-[3-(trifluoromethyl)phenyl]piperazinyl | MH⁺ = 557.9<br>rt = 2.58<br>MS5 |
| 29 | 2-Cl | 4-Cl | (1R, 2R, 3R, 5S) pinanylamino (chiral) | MH⁺ = 481.0<br>rt = 2.65<br>MS5 |
| 30 | 2-Cl | 4-Cl | —(CH₂)₂—(4-F-C₆H₄) | MH⁺ = 466.9<br>rt = 2.41<br>MS5 |

TABLE 2-continued (I)

[Structure: pyrrole with N-Me, 2-aryl (R6,R7), 3-aryl (R3,R4), and C(=O)NR1R2 at position 5]

| Compound No. | R3, R4 | R6, R7 | NR1R2 | Characterization Condition |
|---|---|---|---|---|
| 31 | 2-Cl | 4-Cl | —NH—CH(Me)—phenyl (racemic) | MH+ = 448.9, rt = 2.46, MS5 |
| 32 | 2-Cl | 4-Cl | piperazinyl-(4-chlorophenyl) | MH+ = 523.9, rt = 2.56, MS5 |
| 33 | 2-Cl | 4-Cl | (1R, 2S, 5R) —NH—CH2— bicyclic terpene (chiral) | MH+ = 481.0, rt = 2.67, MS5 |
| 34 | 2-Cl | 4-Cl | —NH—CH2—(4-chlorophenyl) | MH+ = 468.9, rt = 2.45, MS5 |
| 35 | 2-Cl | 4-Cl | —NH—CH2—cyclohexyl | MH+ = 441.0, rt = 2.55, MS5 |
| 36 | 2-Cl | 4-Cl | —NH—C(Me)(Me)—CH2—phenyl | MH+ = 477.0, rt = 2.53, MS5 |
| 37 | 2-Cl | 4-Cl | —NH—CH2—CH(phenyl)2 | MH+ = 524.9, rt = 2.49, MS5 |
| 38 | 2-Cl | 4-Cl | 4-hydroxy-4-phenylpiperidin-1-yl | MH+ = 504.9, rt = 2.38, MS5 |
| 39 | 2-Cl | 4-Cl | 4-hydroxy-4-(4-chlorophenyl)piperidin-1-yl | MH+ = 538.9, rt = 2.41, MS5 |

TABLE 2-continued (I)

| Compound No. | R₃, R₄ | R₆, R₇ | NR₁R₂ | Characterization Condition |
|---|---|---|---|---|
| 40 | 2-Cl | 4-Cl | —N(piperazine)N—C(=O)—(tetrahydrofuran-2-yl) | MH⁺ = 511.9<br>rt = 2.24<br>MS5 |
| 41 | 2-Cl | 4-Cl | —NH—CH₂—phenyl | MH⁺ = 434.9<br>rt = 2.44<br>MS5 |
| 42 | 2-Cl | 4-Cl | —NH—(CH₂)₃—phenyl | MH⁺ = 463.0<br>rt = 2.46<br>MS5 |
| 43 | 2-Cl | 4-Cl | —NH—(CH₂)₂—phenyl | MH⁺ = 448.9<br>rt = 2.45<br>MS5 |
| 44 | 2-Cl | 4-Cl | —NH-(1R)-exo-1,7,7-trimethylbicyclo[2.2.1]heptan-2-yl, chiral | MH⁺ = 481.0<br>rt = 2.65<br>MS5 |
| 45 | 2-Cl | 4-Cl | —N(piperazine)N—(4-CF₃-phenyl) | MH⁺ = 557.9<br>rt = 2.59<br>MS5 |
| 46 | 2-Cl | 4-Cl | —NH-(indan-2-yl) | MH⁺ = 460.9<br>rt = 2.45<br>MS5 |
| 47 | 2-Cl | 4-Cl | —NH-(2-hydroxycyclohexyl) (cis + trans) | MH⁺ = 443.0<br>rt = 2.27<br>MS5 |
| 48 | 2-Cl | 4-Cl | —N(1-methylpiperidin-4-yl)—NH—C(=O)—CF₃ | MH⁺ = 523.9<br>rt = 2.36<br>MS5 |
| 49 | 2-Cl | 4-Cl | —N(piperidinyl with 4-CN and 4-phenyl) | MH⁺ = 513.9<br>rt = 2.49<br>MS5 |

TABLE 2-continued (I)

| Compound No. | R₃, R₄ | R₆, R₇ | NR₁R₂ | Characterization Condition |
|---|---|---|---|---|
| 50 | 2-Cl | 4-Cl | —NH—(4-piperidinyl)-N-CH₂-phenyl | MH⁺ = 518.0<br>rt = 2.04<br>MS5 |
| 51 | 2-Cl | 4-Cl | piperazinyl-N-CH₂-(4-Cl-phenyl) | MH⁺ = 537.9<br>rt = 2.09<br>MS5 |
| 52 | 2-Cl | 4-Cl | —NH—(4,4-dimethylcyclohexyl) | MH⁺ = 455.0<br>rt = 2.54<br>MS5 |
| 53 | 2-Cl | 4-Cl | —NH—(CH₂)₃—CF₃ | MH⁺ = 454.9<br>rt = 2.43<br>MS5 |
| 54 | 2-Cl | 4-Cl | N-(4-(C(O)-nPr)-4-phenyl-piperidinyl) | MH⁺ = 558.9<br>rt = 2.61<br>MS5 |
| 55 | 2-Cl | 4-Cl | —NH—(CH₂)₂-(2-Me-indol-3-yl) | MH⁺ = 501.9<br>rt = 2.41<br>MS5 |
| 56 | 2-Cl | 4-Cl | piperazinyl-N-CH₂-C(O)-N-pyrrolidinyl | MH⁺ = 525.0<br>rt = 2.01<br>MS5 |
| 57 | 2-Cl | 4-Cl | —NH—CH(Me)—(4-Cl-phenyl) racemic | MH⁺ = 482.9<br>rt = 2.49<br>MS5 |
| 58 | 2-Cl | 4-Cl | —NH—(CH₂)₂—(cyclohex-1-enyl) | MH⁺ = 453.0<br>rt = 2.53<br>MS5 |
| 59 | 2-Cl | 4-Cl | piperazinyl-N-CH₂-C(O)-NH—iPr | MH⁺ = 513.0<br>rt = 1.99<br>MS5 |
| 60 | 2-Cl | 4-Cl | —NH—(CH₂)₂—tBu | MH⁺ = 429.0<br>rt = 2.49<br>MS5 |
| 61 | 2-Cl | 4-Cl | —NH—(CH₂)₂—N-pyrrolyl | MH⁺ = 437.9<br>rt = 2.38<br>MS5 |

TABLE 2-continued (I)

| Compound No. | R₃, R₄ | R₆, R₇ | NR₁R₂ | Characterization Condition |
|---|---|---|---|---|
| 62 | 2-Cl | 4-Cl | —NH—CH₂—(adamantyl) | MH⁺ = 493.0<br>rt = 2.63<br>MS5 |
| 63 | 2-Cl | 4-Cl | (N-methylpiperazinyl)—CH₂—(benzodioxole) | MH⁺ = 547.9<br>rt = 2.04<br>MS5 |
| 64 | 2-Cl | 4-Cl | —NH—CH₂—(2-CF₃-phenyl) | MH⁺ = 502.9<br>rt = 2.52<br>MS5 |
| 65 | 2-Cl | 4-Cl | —NH—(norbornyl) (endo) | MH⁺ = 453.0<br>rt = 2.55<br>MS5 |
| 66 | 2-Cl | 4-Cl | —NH—C*H(CH₂Ph)(CH₂—OMe) Chiral (S) | MH⁺ = 478.9<br>rt = 2.34<br>MS5 |
| 67 | 2-Cl | 4-Cl | —NH—CH₂—(benzothiophen-3-yl) | MH⁺ = 490.9<br>rt = 2.49<br>MS5 |
| 68 | 2-Cl | 4-Cl | —NH—C*H(CH₂—OMe)(CH₂Ph) (S) chiral | MH⁺ = 492.9<br>rt = 2.46<br>MS5 |
| 69 | 2-Cl | 4-Cl | (4-phenyl-4-acetyl-piperidin-1-yl) | MH⁺ = 530.9<br>rt = 2.45<br>MS5 |

TABLE 2-continued (I)

| Compound No. | R₃, R₄ | R₆, R₇ | NR₁R₂ | Characterization Condition |
|---|---|---|---|---|
| 70 | 2-Cl | 4-Cl | —NH— cyclohexyl —C(O)OEt (racemic, cis) | MH⁺ = 498.9<br>rt = 2.54<br>MS5 |
| 71 | 2-Cl | 4-Cl | N-methyl-piperidin-4-yl —C(O)—phenyl | MH⁺ = 516.9<br>rt = 2.49<br>MS5 |
| 72 | 2-Cl | 4-Cl | —NH—C(Me)(CH₂Ph)—C(O)OMe (racemic) | MH⁺ = 520.9<br>rt = 2.51<br>MS5 |
| 73 | 2-Cl | 4-Cl | —NH—(CH₂)₂—S-tBu | MH⁺ = 460.9<br>rt = 2.45<br>MS5 |
| 74 | 2-Cl | 4-Cl | —NH—CH₂—(cyclohexyl)—CN (cis) | MH⁺ = 466.0<br>rt = 2.35<br>MS5 |
| 75 | 2-Cl | 4-Cl | —NH—CH(C(O)OCH₃)(CH₂-indol-3-yl) (racemic) | MH⁺ = 545.9<br>rt = 2.43<br>MS5 |
| 76 | 2-Cl | 4-Cl | —NH—CH(C(O)NH₂)(CH₂Ph) (chiral) | MH⁺ = 491.9<br>rt = 2.27<br>MS5 |

TABLE 2-continued (I) [Structure: pyrrole with N-Me, C(=O)-NR₁R₂ at position 2, and two substituted phenyl rings bearing R₃, R₄ and R₆, R₇]

| Compound No. | R₃, R₄ | R₆, R₇ | NR₁R₂ | Characterization Condition |
|---|---|---|---|---|
| 77 | 2,4-diCl | 4-Cl | —NH—(bicyclic pinanyl with two CH₃) (1R) | MH⁺ = 500.9<br>rt = 2.61<br>MS5 |
| 79 | 2,4-diCl | 4-Cl | —NH—cyclohexyl-Me racemic (cis + trans) | MH⁺ = 474.9<br>rt = 2.47<br>MS5 |
| 80 | 2,4-diCl | 4-Cl | —NH—cycloheptyl | MH⁺ = 474.9<br>rt = 2.45<br>MS5 |
| 81 | 2,4-diCl | 4-Cl | —NH—cyclohexyl | MH⁺ = 460.9<br>rt = 2.38<br>MS5 |
| 82 | 2-Cl | 4-Cl | —NH—cycloheptyl | MH⁺ = 441.0<br>rt = 2.49<br>MS5 |
| 83 | 2-Cl | 4-Cl | —NH—norbornyl racemic (eco) | MH⁺ = 439.0<br>rt = 2.46<br>MS5 |

The compounds of formula (I) have very good in vitro affinity ($IC_{50} \leq 5.10^{-7}$M) for the $CB_1$ cannabinoid receptors, under the experimental conditions described by M. Rinaldi-Carmona et al. (FEBS Letters, 1994, 350, 240-244).

The antagonist nature of the compounds of formula (I) was demonstrated by the results obtained in the models of adenylate cyclase inhibition as described in M. Rinaldi-Carmona et al., J. Pharmacol. Exp. Ther., 1996, 278, 871-878 and M. Bouaboula et al., J. Biol. Chem., 1997, 272, 22330-22339.

The toxicity of the compounds of formula (I) is compatible with their use as medicaments.

Thus, according to another of its aspects, a subject of the invention is medicaments for human or veterinary medicine, which comprise a compound of formula (I) or a solvate or a hydrate of the compound of formula (I).

Thus, the compounds according to the invention may be used in man or animals, in the treatment or prevention of diseases involving the $CB_1$ cannabinoid receptors.

According to another of its aspects, the present invention relates to the use of a compound of formula (I), or a pharmaceutically acceptable salt, solvate or hydrate thereof, for the preparation of medicaments intended for treating or preventing diseases involving the $CB_1$ cannabinoid receptors.

For example, and in a non-limiting manner, the compounds of formula (I) are useful as psychotropic medicaments, especially for treating psychiatric disorders including anxiety, depression, mood disorders, insomnia, delirium disorders, obsessive disorders, psychoses in general, schizophrenia, attention and hyperactivity disorders (AHD) in hyperkinetic children (MBD), and also for treating disorders associated with the use of psychotropic substances, especially in the case of substance abuse and/or substance dependency, including alcohol dependency and nicotine dependency.

The compounds of formula (I) according to the invention may be used as medicaments for treating migraine, stress, diseases of psychosomatic origin, panic attacks, epilepsy, movement disorders, in particular dyskinesia or Parkinson's disease, trembling and dystonia.

The compounds of formula (I) according to the invention may also be used as medicaments in the treatment of memory deficit, cognitive disorders, in particular in the treatment of senile dementia and Alzheimer's disease, and also in the treatment of attention or consciousness disorders. Furthermore, the compounds of formula (I) may be useful as neuroprotective agents, in the treatment of ischemia, cranial trauma and the treatment of neurodegenerative diseases: including chorea, Huntington's chorea and Tourette's syndrome.

The compounds of formula (I) according to the invention may be used as medicaments in the treatment of pain: neuropathic pain, acute peripheral pain, chronic pain of inflammatory origin.

The compounds of formula (I) according to the invention may be used as medicaments in the treatment of appetite disorders, appetence disorders (for sugars, carbohydrates, drugs, alcohol or any appetizing substance) and/or eating behavior, especially as anorexigenic agents or for the treatment of obesity or bulimia, and also for the treatment of type II diabetes or non-insulin-dependent diabetes and for the treatment of dyslipidemia and metabolic syndrome. Thus, the compounds of formula (I) according to the invention are useful in the treatment of obesity and of the risks associated with obesity, especially the cardiovascular risks. Furthermore, the compounds of formula (I) according to the invention may be used as medicaments in the treatment of gastrointestinal disorders, diarrheic disorders, ulcers, vomiting, vesical and urinary disorders, disorders of endocrine origin, cardiovascular disorders, hypotension, hemorrhagic shock, septic shock, chronic cirrhosis of the liver, chronic hepatic encephalopathy, asthma, chronic bronchitis and chronic obstructive bronchopneumopathy, Raynaud's syndrome, glaucoma, fertility disorders, inflammatory phenomena, immune system diseases, in particular autoimmune and neuroinflammatory diseases such as rheumatoid arthritis, rectional arthritis, diseases resulting in demyelinization, multiple sclerosis, infectious and viral diseases such as encephalitis, strokes, and also as medicaments for anticancer chemotherapy and for the treatment of Guillain-Barré syndrome and for the treatment of bone diseases and osteoporosis.

According to the present invention, the compounds of formula (I) are most particularly useful for treating psychotic disorders, in particular schizophrenia; attention and hyperactivity disorders (AHD) in hyperkinetic children (MBD), for the treatment of appetite disorders and obesity, for the treatment of memory deficiency and cognitive deficiency; for the treatment of alcohol dependency or nicotine dependency, i.e. for weaning from alcohol and for weaning from tobacco; and for the treatment of dyslipidemia and metabolic syndrome.

More particularly, the compounds of formula (I) according to the present invention are useful in the treatment and prevention of appetite disorders, metabolic disorders, gastrointestinal disorders, inflammatory phenomena, immune system diseases, psychotic disorders, alcohol dependency and nicotine dependency. According to one of its aspects, the present invention relates to the use of a compound of formula (I) or the pharmaceutically acceptable salts thereof and solvates or hydrates thereof for the treatment of the disorders and diseases indicated above.

The compound according to the invention is generally administered in a dosage unit.

The said dosage units are preferably formulated in pharmaceutical compositions in which the active principle is mixed with a pharmaceutical excipient.

Thus, according to another of its aspects, the present invention relates to pharmaceutical compositions containing, as active principle, a compound of formula (I), one of the pharmaceutically acceptable salts thereof or one of the solvates thereof.

The compound of formula (I) above and the pharmaceutically acceptable salts or solvates thereof may be used in daily doses of from 0.01 to 100 mg per kg of body weight of the mammal to be treated, and preferably in daily doses of from 0.02 to 50 mg/kg. in man, the dose may preferably range from 0.05 to 4000 mg per day and more particularly from 0.1 to 1000 mg per day depending on the age of the individual to be treated or the type of treatment, i.e. prophylactic or curative. Although these dosages are examples of average situations, there may be particular cases in which higher or lower dosages are appropriate, and such dosages also form part of the invention. According to the usual practice, the dosage that is appropriate for each patient is determined by the doctor according to the mode of administration and the age, weight and response of the said patient.

In the pharmaceutical compositions of the present invention for oral, sublingual, inhaled, subcutaneous, intramuscular, intravenous, transdermal, local or rectal administration, the active principle may be administered in a unit administration form, as a mixture with standard pharmaceutical supports, to man and animals. The appropriate unit administration forms include oral forms such as tablets, gel capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

In the pharmaceutical compositions of the present invention, the active principle is generally formulated in dosage units containing from 0.05 to 1000 mg, advantageously from 0.1 to 500 mg and preferably from 1 to 200 mg of the said active principle per dosage unit for daily administrations.

By way of example, a unit administration form of a compound according to the invention in tablet form may comprise the following components:

| | |
|---|---:|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Via the oral route, the dose or active principle administered per day may reach 0.01 to 100 mg/kg and preferably 0.02 to 50 mg/kg, in one or more dosage intakes.

There may be particular cases in which higher or lower dosages are appropriate; such dosages do not depart from the context of the invention. According to the usual practice, the dosage that is appropriate for each patient is determined by the doctor according to the mode of administration and the weight and response of the said patient.

According to another of its aspects, the present invention also relates to a method for treating the pathologies indicated above, which comprises the administration to a patient of an effective dose of a compound according to the invention, or hydrates or solvates thereof.

According to the present invention, a compound of formula (I) may be combined with another active principle chosen from one of the following therapeutic classes:

an angiotensin II $AT_1$ receptor antagonist, alone or combined with a diuretic;
a converting enzyme inhibitor, alone or combined with a diuretic or a calcium antagonist;
a calcium antagonist;
a beta-blocker, alone or combined with a diuretic or a calcium antagonist;
an antihyperlipaemiant or an antihypercholesterolaemiant agent;
an antidiabetic agent;
another anti-obesity agent.

Thus, a subject of the present invention is also pharmaceutical compositions containing in combination a compound of formula (I) and another active principle chosen from one of the following therapeutic classes:

an angiotensin II $AT_1$ receptor antagonist, alone or combined with a diuretic or a calcium antagonist;
a converting enzyme inhibitor, alone or combined with a diuretic;
a calcium antagonist;
a beta-blocker, alone or combined with a diuretic or a calcium antagonist;
an antihyperlipaemiant or an antihypercholesterolaemiant agent;
an antidiabetic agent;
another anti-obesity agent.

The term "angiotensin II $AT_1$ receptor antagonist" means a compound such as candesartan cilexitil, eprosartan, irbesartan, losartan potassium, olmesartan medoxomil, telmisartan and valsartan, each of these compounds itself possibly being combined with a diuretic such as hydrochlorothiazide.

The term "converting enzyme inhibitor" means a compound such as alacepril, benazepril, captopril, cilazapril, enalapril, enalaprilat, fosinopril, imidapril, lisinopril, moexipril, perindopril, quinapril, ramipril, spirapril, temocapril, trandolapril and zofenopril, each of these compounds itself possibly being combined with a diuretic such as hydrochlorothiazide or indapamide or with a calcium antagonist such as amlodipine, diltiazem, felodipine or verapamil.

The term "calcium antagonist" means a compound such as amlodipine, aranidipine, benidipine, bepridil, cilnidipine, diltiazem, efonidipine hydrochloride ethanol, fasudil, felodipine, isradipine, lacidipine, lercanidipine hydrochloride, manidipine, mibefradil hydrochloride, nicardipine, nifedipine, nilvadipine, nimodipine, nisoldipine, nitrendipine, terodiline and verapamil.

The term "beta-blocker" means a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propanolol, salmeterol, sotalol, talinolol, tertatolol, tilisolol, timolol, xamoterol and xibenolol.

The term "antihyperlipaemiant or antihypercholesterolaemiant agent" means a compound chosen from fibrates such as alufibrate, beclobrate, bezafibrate, ciprofibrate, clinofibrate, clofibrate, etofibrate and fenofibrate; statins (HMG-CoA reductase inhibitors), such as atorvastatin, fluvastatin sodium, lovastatin, pravastatin, rosuvastatin or simvastatin, or a compound such as acipimox, aluminum nicotinate, azacosterol, cholestyramine, dextrothyroxine, meglutol, niceritrol, nicoclonate, nicotinic acid, beta-sitosterin or tiadenol. More particularly, a subject of the present invention is a pharmaceutical composition containing in combination a compound of formula (I) and atorvastatin or pravastatin, or, preferably, a compound of formula (I) and simvastatin.

The term "antidiabetic agent" means a compound belonging to one of the following classes: sulfonylureas, biguanidines, alpha-glucosidase inhibitors, thiazolidinediones, metiglinides, such as acarbose, acetohexamide, carbutamide, chlorpropamide, glibenclamide, glibornuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone and voglibose.

The term "another anti-obesity agent" means a compound such as amfepramone, benfluorex, benzphetamine, indanorex, mazindole, mefenorex, methamphetamine or D-norpseudoephedrine, or another cannabinoid $CB_1$ receptor antagonist.

Most particularly, a subject of the present invention is a pharmaceutical composition containing in combination a compound of formula (I) and an angiotensin II $AT_1$ receptor antagonist, especially irbesartan, losartan or valsartan.

According to another aspect of the invention, the compound of formula (I) and the other combined active principle may be administered simultaneously, separately or sequentially over time.

The term "use separately" means the administration, at the same time, of the two compounds of the composition according to the invention, each included in a separate pharmaceutical form.

The term "use sequentially over time" means the successive administration of the first compound of the composition according to the invention, included in one pharmaceutical form, and then of the second compound of the composition according to the invention, included in a separate pharmaceutical form.

What is claimed is:
1. A compound of formula (IIa):

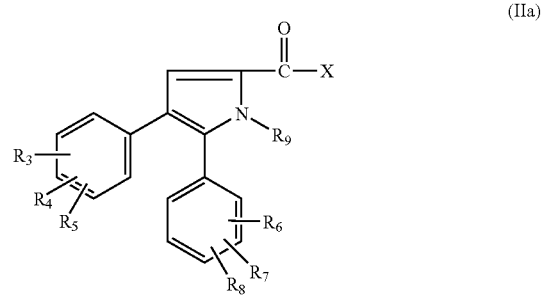

in which:

X represents a halogen atom or a hydroxyl, $(C_1-C_4)$alkoxy or benzyloxy group;

$R_3$ is a halogen atom, a $(C_1-C_6)$alkyl, $(C_1-C_6)$alkoxy or trifluoromethyl group or a group $S(O)_n$Alk;

$R_4$, $R_5$, $R_6$, $R_7$ and $R_8$ represent, independently of each other, a hydrogen or halogen atom, a $(C_1-C_6)$alkyl, $(C_1-C_6)$alkoxy or trifluoromethyl group or a group $S(O)_n$Alk;

$R_9$ represents a $(C_1-C_4)$alkyl;

Alk represents a $(C_1-C_4)$alkyl; and n represents 0, 1 or 2.

2. A method for a treatment of alcohol or nicotine dependency in a patient comprising administering to said patient a therapeutically effective amount of a compound of formula (I) or a salt thereof:

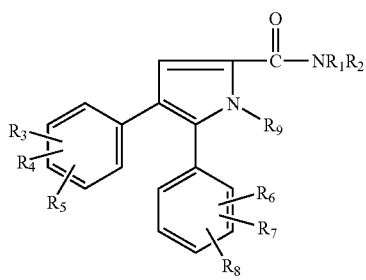

(I)

in which:

$R_1$ represents hydrogen or a $(C_1-C_4)$alkyl;

$R_2$ represents:
- a $(C_3-C_{10})$alkyl group, which is unsubstituted or substituted with a trifluoromethyl group;
- a non-aromatic $C_3-C_{12}$ carbocyclic radical, which is unsubstituted or substituted one or more times with a $(C_1-C_4)$alkyl, hydroxyl, cyano or $(C_1-C_4)$alkoxy group or a group $COR_{12}$;
- an indanyl;
- a 1,2,3,4-tetrahydro-1- or -2-naphthyl;
- a monooxygen or monosulfur heterocyclic radical of 5 to 7 atoms, which is unsubstituted or substituted one or more times with a $(C_1-C_4)$alkyl group;
- a mononitrogen heterocyclic radical of 5 to 7 atoms, which is unsubstituted or substituted one or more times with a $(C_1-C_4)$alkyl group, the nitrogen atom moreover being substituted with a $(C_1-C_4)$alkyl, phenyl, benzyl, $(C_1-C_4)$alkoxycarbonyl or $(C_1-C_4)$alkanoyl group, the phenyl or benzyl groups being unsubstituted or substituted one or more times with a halogen atom or a $(C_1-C_4)$alkyl, trifluoromethyl, hydroxyl or $(C_1-C_4)$alkoxy group;
- a benzothiophenyl or an indolyl, the said radicals being unsubstituted or substituted one or more times with a $(C_1-C_4)$alkyl group;
- a $(C_1-C_3)$alkylene group bearing a non-aromatic $C_3-C_{10}$ carbocyclic radical, which is unsubstituted or substituted one or more times with a $(C_1-C_4)$alkyl, hydroxyl, $(C_1-C_4)$alkoxy or cyano group or a group $COR_{12}$;
- a $(C_1-C_3)$alkylene group bearing a monooxygen, monosulfur or mononitrogen heteroaromatic or non-heteroaromatic heterocyclic radical of 5 to 7 atoms, which is unsubstituted or substituted one or more times with a $(C_1-C_4)$alkyl group;
- a $(C_1-C_3)$alkylene group bearing an indolyl or benzothiophenyl radical, the said radical being unsubstituted or substituted one or more times with a $(C_1-C_4)$ alkyl group and the alkylene being unsubstituted or substituted with a hydroxyl, methyl or methoxy group or with a group $COR_{12}$;
- a $(C_1-C_3)$alkylene group bearing a $(C_1-C_4)$alkylthio group;
- a phenylalkylene group in which the alkylene is $(C_1-C_3)$, which is unsubstituted or substituted on the alkylene with one or more methyl, hydroxyl, hydroxymethyl, methoxy or methoxymethyl groups, or a group $COR_{12}$, and which is unsubstituted on the phenyl or substituted on the phenyl with one or more identical or different substituents chosen from a halogen atom and a $(C_1-C_4)$alkyl, trifluoromethyl, $(C_1-C_4)$alkoxy or trifluoromethoxy group;
- a benzhydryl or benzhydrylmethyl group; and
- a group $NR_{10}R_{11}$;

or $R_1$ and $R_2$, together with the nitrogen atom to which they are attached, constitute:
- either a piperazin-1-yl or 1,4-diazepan-1-yl radical 4-substituted with a phenyl, benzyl, benzodioxolyl, benzodioxolylmethyl or tetrahydrofurylcarbonyl group or with a group $COR_{12}$ or $CH_2COR_{12}$;
- or a piperid-1-yl or pyrrolidin-1-yl radical mono- or gem-disubstituted with one or two groups chosen from a phenyl, benzyl, piperid-1-yl, pyrrolidin-1-yl, $(C_1-C_4)$alkyl, hydroxyl or cyano group and a group $COR_{12}$, $NR_{13}R_{14}$, $NHCOR_{15}$ or $CH_2COR_{12}$;
- the phenyl or benzyl groups being unsubstituted or substituted with one or more substituents independently chosen from a halogen atom, and a methyl, trifluoromethyl, hydroxyl or $(C_1-C_4)$alkoxy group;

$R_3$, $R_4$, $R_5$, $R_6$, $R_7$ and $R_8$ represent, independently of each other, a hydrogen or halogen atom, a $(C_1-C_6)$alkyl, $(C_1-C_6)$alkoxy or trifluoromethyl group or a group $S(O)_n$Alk;

$R_9$ represents a $(C_1-C_4)$alkyl group;

$R_{10}$ represents a hydrogen atom or a methyl group;

$R_{11}$ represents a $(C_3-C_6)$alkyl, phenyl or $(C_3-C_{10})$cycloalkyl group, the said phenyl and cycloalkyl groups being unsubstituted or substituted with one or more substituents independently chosen from a halogen atom and a $(C_1-C_4)$alkyl or trifluoromethyl group;

or $R_{10}$ and $R_{11}$, together with the nitrogen atom to which they are attached, constitute a saturated or unsaturated, bridged or non-bridged heterocyclic radical of 4 to 11 atoms, possibly comprising a spirane carbon and possibly containing a second hetero atom chosen from O and N, the said radical being unsubstituted or substituted one or more times with a hydroxyl, $(C_1-C_4)$alkyl or $(C_1-C_4)$alkoxycarbonyl group or with a phenyl group that is unsubstituted or substituted with one or more substituents independently chosen from a halogen atom and a $(C_1-C_4)$alkyl group;

$R_{12}$ represents a $(C_1-C_4)$alkyl, phenyl, benzyl, $(C_1-C_4)$ alkoxy or trifluoromethyl group or a group $NR_{13}R_{14}$;

$R_{13}$ and $R_{14}$ each independently represent a hydrogen atom or a $(C_1-C_4)$alkyl group or, together with the nitrogen atom to which they are attached, constitute a radical chosen from azetidinyl, pyrrolidinyl, piperazinyl, piperidyl and azepinyl;

$R_{15}$ represents a $(C_1-C_4)$alkyl or trifluoromethyl group;

n represents 0, 1 or 2; and

Alk represents a $(C_1-C_4)$alkyl group.

3. The method according to claim 2, wherein the compound of formula (I) is having:

R$_1$ represents hydrogen and R$_2$ represents a group NR$_{10}$R$_{11}$ in which R$_{10}$ and R$_{11}$, together with the nitrogen atom to which they are attached, constitute a saturated heterocyclic radical of 5 to 11 carbon atoms, which is unsubstituted or substituted one or more times with a (C$_1$-C$_4$)alkyl;

or R$_1$ and R$_2$, together with the nitrogen atom to which they are attached, constitute a piperid-1-yl radical gem-disubstituted with a phenyl, benzyl, pyrrolidin-1-yl or piperid-1-yl group and with a cyano, (C$_1$-C$_3$)alkanoyl or aminocarbonyl group;

or R$_1$ and R$_2$ together represent a piperazin-1-yl group 4-substituted with a benzyl, which is itself unsubstituted or substituted with a halogen atom;

R$_3$, R$_4$, R$_5$, R$_6$, R$_7$ and R$_8$ represent, independently of each other, a hydrogen or halogen atom or a methoxy group; and R$_9$ represents a (C$_1$-C$_4$)alkyl group;

or a salt thereof.

4. The method according to claim 2, wherein the compound of formula (I) is having:

R$_1$ represents hydrogen and R$_2$ represents a piperid-1-yl radical or a (C$_1$-C$_3$)alkylene radical substituted with a phenyl and with a methoxy or methoxycarbonyl group;

or R$_1$ and R$_2$, together with the nitrogen atom to which they are attached, represent a piperid-1-yl radical 4-gem-disubstituted with a phenyl or piperid-1-yl group and with an acetyl, aminocarbonyl or cyano group;

or R$_1$ and R$_2$ together represent a piperazin-1-yl group 4-substituted with a benzyl, which is itself unsubstituted or substituted with a halogen atom;

R$_6$ is a 4-chloro or a 4-methoxy and R$_3$ and R$_4$ represent 2,4-dichloro or 2-chloro, R$_5$, R$_7$ and R$_8$ representing a hydrogen atom;

R$_9$ represents a methyl group;

or a salt thereof.

5. The method according to claim 2, wherein the compound of formula (I) is chosen from:

4-(2,4-dichlorophenyl)-5-(4-methoxyphenyl)-1-methyl-N-piperid-1-yl-1H-pyrrole-2-carboxamide;

5-(4-chlorophenyl)-4-(2,4-dichlorophenyl)-1-methyl-N-piperid-1-yl-1H-pyrrole-2-carboxamide;

1-(1-((5-(4-chlorophenyl)-4-(2,4-dichlorophenyl)-1-methyl-1H-pyrrol-2-yl)carboxyl)-4-phenylpiperid-4-yl)ethanone;

1-{[4-(2-chlorophenyl)-5-(4-chlorophenyl)-1-methyl-1H-pyrrol-2-yl]carbonyl}-4-phenylpiperidine-4-carbonitrile;

1-(4-chlorobenzyl)-4-{[4-(2-chlorophenyl)-5-(4-chlorophenyl)-1-methyl-1H-pyrrol-2-yl]carbonyl}piperazine;

N-(1-benzyl-2-methoxyethyl)-4-(2-chlorophenyl)-5-(4-chlorophenyl)-1-methyl-1H-pyrrole-2-carboxamide;

methyl 1-{[4-(2-chlorophenyl)-5-(4-chlorophenyl)-1-methyl-1H-pyrrol-2-yl]carbonyl}-α-methylphenylalaninate; and 1'-{[5-(4-chlorophenyl)-4-(2,4-dichlorophenyl)-1-methyl-1H-pyrrol-2-yl]carbonyl}-1,4'-bipiperidine-4'-carboxamide;

or a salt thereof.

* * * * *